United States Patent [19]

Saint-Leger et al.

[11] Patent Number: 5,141,874
[45] Date of Patent: Aug. 25, 1992

[54] METHOD FOR THE DIFFERENTIAL COLORATION OF SKIN CELLS AND THEIR NUCLEII

[75] Inventors: Didier Saint-Leger, Paris; Anne-Marie Francois, Croissy-Beaubourg; Jean-Luc Leveque, Le Raincy, all of France

[73] Assignee: L'Oreal, Paris, France

[21] Appl. No.: 441,543

[22] Filed: Nov. 27, 1989

[30] Foreign Application Priority Data

Nov. 30, 1988 [FR] France ............... 88 15684

[51] Int. Cl.⁵ ............................ G01N 21/75
[52] U.S. Cl. ........................ 436/166; 436/169; 436/800; 424/2; 424/3; 424/7.1
[58] Field of Search ........ 436/536, 800, 169, 535, 436/528, 166; 424/3, 7.1, 2

[56] References Cited

U.S. PATENT DOCUMENTS

| | | | |
|---|---|---|---|
| 3,899,297 | 8/1975 | Hirschfeld | 424/3 |
| 4,137,299 | 1/1979 | DiMaggio, Jr. | 424/3 |
| 4,146,604 | 3/1979 | Kleinerman | 424/3 |
| 4,166,105 | 8/1979 | Hirschfeld | 424/3 |
| 4,239,495 | 12/1980 | Gindler et al. | 424/3 |
| 4,595,582 | 6/1986 | Balogh et al. | 424/3 |
| 4,665,024 | 5/1987 | Mansour | 436/800 |
| 4,714,606 | 12/1987 | Kass | 424/7.1 |

FOREIGN PATENT DOCUMENTS 1245742 9/1971 United Kingdom .

OTHER PUBLICATIONS

Chemical Abstracts, vol. 90, No. 19, May 7, 1979, p. 262, No. 148039y, Giorgio et al.
Chemical Abstracts, vol. 108, No. 3, Jan. 18, 1988, p. 301, No. 18665d, Levame et al.

*Primary Examiner*—James C. Housel
*Assistant Examiner*—Maureen M. Wallenhorst
*Attorney, Agent, or Firm*—Cushman, Darby & Cushman

[57] ABSTRACT

A method for the differential coloration of skin cells and their nucleii fixed on a transparent or translucent adhesive support, involves successively immersing the cells in two baths, A and B, bath A containing methyl blue or a derivative of methyl blue and bath B containing methyl blue, and/or methylene blue and rhodamine B or a derivative of rhodamine, and then rinsing and drying the support. This method of coloration can be used in the diagnosis of inflammatory skin conditions.

10 Claims, No Drawings

METHOD FOR THE DIFFERENTIAL COLORATION OF SKIN CELLS AND THEIR NUCLEII

The present invention relates to a method for the differential coloration of skin cells and their nucleii, which is particularly useful when the cell is fixed on an adhesive support.

It is known to use adhesive supports for the removal of cells, particularly for the removal of skin cells. Numerous adhesive supports are sold commercially. For example, those sold under the trade names "D'SQUAME" by Cutech Company, "TESA FILM" by Beiersdorf Company and "SCOTCH" by 3M Company can be cited. These adhesive supports are generally in the form of transparent or translucent ribbons or strips.

If it is sought to observe the removed cells on these supports, it is necessary to carry out a coloration of said cells; said coloration must be different from that of the nucleii if it is sought to distinguish the nucleii in the cells, either that their color is different or that the intensity of the coloration is different. The problem is then to find a method for differential coloration of the cells and the nucleii which does not interfere with the support, either by destroying it or by coloring it.

Tests have been carried out with numerous coloring agents which are acceptable for the coloration of cells or nucleii such as those cited, for example, in "Histochimie normale et pathologique" by Ganter and Gilles, 1969, Gauthier Villards publishers, and it has never been possible to show the nucleii because the coloring agents interfere with the adhesive support. In accordance with the present invention a method has been found for the differential coloration of the cell and the nucleus which does not interfere with the adhesive support and does not color it.

The present invention relates to a method for the differential coloration of skin cells and their nucleii, with the cells being fixed on a transparent or translucent adhesive support, wherein the adhesive support containing the cells is successively immersed in two baths:

as a first step, immersing said cells in a bath A containing by weight:

0.1 to 10% of at least one coloring agent corresponding to general formula I:

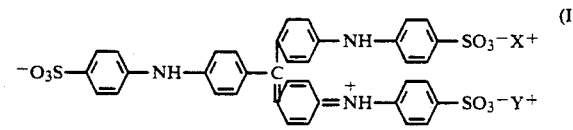

wherein
X$^-$ and Y$^-$ are cations of mineral or organic origin, and preferably sodium,
10 to 80% of at least one water-miscible alcohol, and 20 to 95% water,
with the bath having been brought to a basic pH of between 7.5 and 13.5 by the addition of a mineral or organic base, for example soda or potash, and as a second step, immersing said cells from said first step in a bath B containing by weight:

0.01 to 10% of at least one coloring agent of formula I defined above or even methylene blue, 0.2 to 10% of at least one coloring agent of formula II:

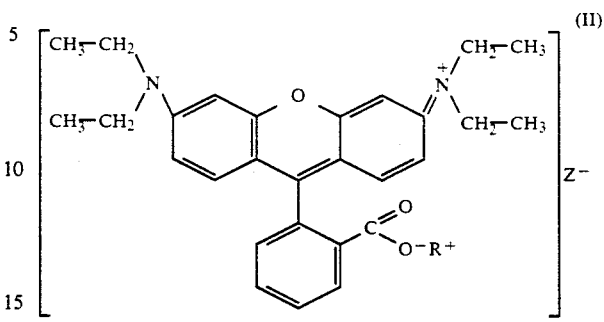

wherein
Z$^-$ is a mineral or organic anion and R is hydrogen or a mineral or organic cation,
5 to 40% of a water-miscible solvent, and
5 to 50% water,
with the bath having been brought to an acid pH of between 2 and 6.5.

In this manner, after coloration, an intact adhesive support is obtained which has not been colored and wherein the cells are colored a pale mauve pink, with the nucleii having substantially a darker shade of the same color.

In accordance with the present invention, the successive use in order of the two baths is necessary. In effect, the use of the two baths in a different order, that is bath B then bath A, or the use of a single bath A or B, results either in the absence of cell coloration or in the absence of the showing of the nucleii.

In bath A and/or B the coloring agent of formula I used is, preferably, methyl blue corresponding to formula I in which X$^+$ and Y$^+$ are Na$^+$.

In bath A, the water-miscible alcohol is preferably ethanol, isopropanol or methanol, with methanol being preferred.

The basic pH of bath A is obtained by addition of soda or potash in an amount such that the final pH is between 7.5 and 13.5. For example, in the case of a bath containing 1% of methyl blue, a final concentration with 0.3N of soda or potash gives excellent results.

In bath B, the coloring agent of formula II used is, preferably, the rhodamine B corresponding to formula II, in which Z$^-$ is Cl$^-$ and R is H.

In bath B, the water-miscible solvent can particularly be a water-miscible alcohol or a mixture of water-miscible alcohols, and preferably a mixture of methanol and ethanol, in any amounts whatever.

The length of time of immersion of the adhesive support in bath A is, preferably, from 5 to 20 minutes, and advantageously approximately 10 minutes. Similarly, the length of time of immersion in bath B is, preferably, from 10 seconds to 10 minutes, and advantageously approximately 2 minutes.

After each bath, the adhesive support is preferably briefly rinsed with water. This water can be tap water or distilled water. The support is then dried using any appropriate means, such as a hair dryer or an oven.

Once dried, the support is not damaged and can then be stuck using its own adhesive onto any material known to the skilled artisan which is suitable for microscopic examination.

In accordance with a preferred embodiment of the invention, baths A and B can contain from 0.01 to 1% of an antioxidizing agent such as, for example, butyl hydroxy toluene or butyl hydroxy anisole, etc.

The method of coloration in accordance with the invention can, more especially, be used in a method for the diagnosis of skin inflammatory conditions. In effect, it is known that, in the case of skins in the normal, and therefore non-pathological, state, the surface cutaneous cells or corneocytes are totally keratinized cells which have no nucleus. Where there is inflammation of the skin, whatever the cause, the acceleration of epidermal cell renewal results in the delivery to the surface of the epidermis of immature cells which still have a nucleus. The percentage of nucleated cells, also called parakeratotic cells, at the surface of the skin is therefore an excellent indication of the severity of the inflammatory condition. For example, a percentage of nucleated cells of:

less than 10% indicates slight inflammation,
from 10 to 30% indicates moderate inflammation,
from 30 to 60% indicates considerable inflammation, and
more than 60% indicates severe inflammation.

Consequently, in order to carry out the diagnosis, the cutaneous surface cells are removed by "stripping" using an adhesive support, and a differential coloration of the cells and the nucleii is carried out using the method of coloration in accordance with the invention. Analysis of the image obtained is then carried out either directly with a microscope or by photography, and the percentage of nucleated cells is determined by counting. In this manner, a quantitative gradation of the severity of the cutaneous inflammation is obtained. Diagnosis using the method of differential coloration in accordance with the present invention is simple and rapid and is not traumatic for the patient. Such a measurement is especially interesting for determining erythemas on black skin and in cases where the inflammation is in a latent condition (dandruff of the scalp). Such a diagnosis enables the effectiveness of treatments, in particular for psoriasis, eczema, mycosis, acne, seborrheic dermatitis, dandruff, contact allergy or solar erythema using anti-inflammatory agents (for example, hydrocortisone and its esters, cortisone, triamcinolone and its derivatives, indomethacin, glycerrhetinic acid, aspirin, dexamethasone, beta methasone, fluocinolone, fluorometholone, piroxicam, diclofenac, silindac, niflumic acid, mefenamic acid, ibuprofen, naproxen, ketoprofen, phenylbutazone, oxyphenbutazone and their derivatives) to be followed in a simple manner.

EXAMPLE

Cutaneous cells from the cheek of a patient with seborrheic dermatitis were removed using an adhesive ribbon sold under the trade name "SCOTCH" by 3M Company.

After removal, the adhesive ribbon was dipped successively:

for 10 minutes in a bath A with a pH of 7.8 containing in % by weight:
water 70%,
methanol 29%,
methyl blue 1%, and then for 2 minutes in a bath B with a pH of 5.8 containing in % by weight:
methanol 30%,
ethanol 10%,
methyl blue 0.25%,
rhodamine B 2.5%, and
water, quantity sufficient for 100%.

After baths A and B, the adhesive ribbon was rinsed with distilled water and then dried using a hair dryer for 3 minutes.

A photograph of an area of the adhesive support prepared in this manner was then taken using a microscope. A photograph was obtained in which the cells were colored a mauve pink and the nucleii appeared in a darker shade of the same color. By counting, it was determined that 80 to 90% of the cutaneous cells were nucleated.

We claim:

1. A method for the differential coloration of skin cells and their nucleii, said cells being fixed on a transparent or translucent adhesive support, wherein the adhesive support containing the cells is successively immersed in two baths:

said method comprising in a first step, immersing said adhesive support containing said cells in a bath A containing by weight:

0.1 to 10% of a coloring agent having formula I $$^{-}O_3S-\underset{}{\bigcirc}-NH-\underset{}{\bigcirc}-C\underset{=NH-\underset{}{\bigcirc}-SO_3^-Y^+}{\overset{-NH-\underset{}{\bigcirc}-SO_3^-X^+}{}} \quad (I)$$

wherein
$X^+$ and $Y^+$ are sodium cations,
10 to 80% of at least one water-miscible alcohol, and
20 to 95% water, said bath A having been brought to a basic pH of between 7.5 and 13.5 by the addition of soda or potash, and in a second step, immersing said adhesive support containing said cells from said first step in a bath B containing by weight:

0.01 to 10% of said coloring agent of formula I defined above,
0.2 to 10% of a coloring agent having formula II:

$$\left[\begin{array}{c}CH_3-CH_2\\ \phantom{C}\diagdown\\ CH_3-CH_2\end{array}\underset{}{N}-\underset{}{\bigcirc}\underset{O}{\overset{}{\underset{}{\bigcirc}}}\underset{}{\bigcirc}=\underset{}{\overset{+}{N}}\diagup\begin{array}{c}CH_2-CH_3\\ \phantom{C}\\ CH_2-CH_3\end{array}\\ \underset{}{\bigcirc}\overset{}{\underset{O-R^+}{\overset{O}{\diagdown}}}\end{array}\right] Z^- \quad (II)$$

wherein
$Z^-$ is a chlorine anion and R is hydrogen,
5 to 40% of a water-miscible solvent, and
5 to 50 % water,
said bath B having been brought to an acid pH of between 2 and 6.5.

2. The method of coloration in accordance with claim 1, wherein, in bath A, the water-miscible alcohol is ethanol, isopropanol or methanol.

3. The method of coloration in accordance with claim 1, wherein, in bath B, the water-miscible solvent is a water-miscible alcohol or a mixture of water-miscible alcohols.

4. The method of claim 3, wherein said mixture of water-miscible alcohols is a mixture of methanol and ethanol.

5. The method of coloration in accordance with claim 1, wherein the length of time of immersion in bath A is from 5 to 20 minutes.

6. The method of claim 1 wherein the length of time of immersion in bath A is approximately 10 minutes.

7. The method of coloration in accordance with claim 1, wherein the length of time of immersion in bath B is from 10 seconds to 10 minutes.

8. The method of claim 1, wherein the length of time of immersion in bath B is approximately 2 minutes.

9. The method of coloration in accordance with claim 1, wherein after removal of the adhesive support from each bath the said adhesive support is rinsed with water and then dried.

10. A method for the diagnosis of an inflammatory skin condition comprising removing cutaneous surface cells of the skin using an adhesive support, immersing, in a first step, said adhesive support containing said cells in a bath A containing by weight 0.1 to 10% of a coloring agent having formula I

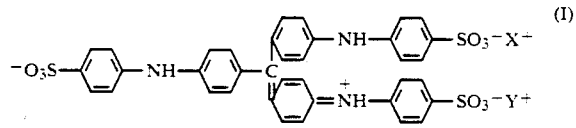

wherein
X$^+$ and Y$^+$ are sodium cations,
10 to 80% of at least one water-miscible alcohol, and
20 to 95% water,
said bath A having been brought to a basic pH of between 7.5 and 13.5 by the addition of soda or potash,
immersing, in a second step, said adhesive support containing said cells from said first step in a bath B containing by weight
0.01 to 10% of said coloring agent of formula I defined above,
0.2 to 10% of a coloring agent having formula II:

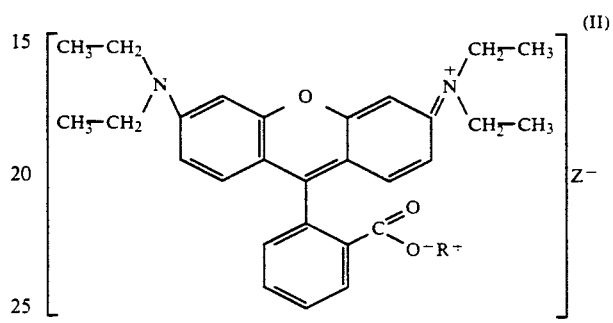

wherein
Z$^-$ is a chlorine anion and R is hydrogen,
5 to 40% of a water-miscible solvent, and
5 to 50% water,
said bath B having been brought to an acid pH of between 2 and 6.5,
analyzing the image obtained on said adhesive support after said second step and
determining the percentage of nucleated cells observed on said adhesive support by counting, thereby providing a quantitative gradation of the severity of cutaneous inflammation.

* * * * *